United States Patent
Arcari et al.

[11] 3,975,389
[45] Aug. 17, 1976

[54] CAFFEINE DERIVATIVES

[75] Inventors: Giuliana Arcari; Pietro De Micheli; Fulvio Luini; Ugo Scarponi, all of Milan, Italy

[73] Assignee: Societa Farmaceutici Italia S.p.A., Milan, Italy

[22] Filed: Sept. 23, 1974

[21] Appl. No.: 508,571

[30] Foreign Application Priority Data
Sept. 26, 1973 Italy .................................. 29406/70

[52] U.S. Cl. .............................. 260/254; 424/253; 260/256
[51] Int. Cl.[2] ..................................... C07D 473/12
[58] Field of Search ........................... 260/256, 254

[56] References Cited
UNITED STATES PATENTS
2,879,271   3/1959   Kallischnigy ...................... 260/256

OTHER PUBLICATIONS
Wagner et al., *Synthetic Organic Chemistry* Wiley & Sons Inc., New York, 1953.

Primary Examiner—Paul M. Coughlan, Jr.
Attorney, Agent, or Firm—Stevens, Davis, Miller & Mosher

[57] ABSTRACT

New derivatives of caffeine are disclosed having the formula:

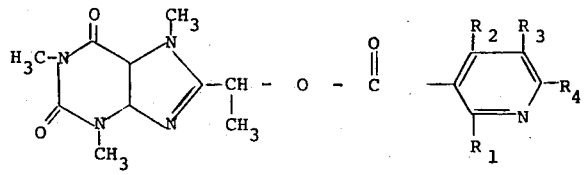

where $R_1$, $R_2$, $R_3$ and $R_4$ are selected from the group consisting of hydrogen, chlorine, bromine, an alkyl or an alkoxy radical containing from 1 to 4 carbon atoms. They are made by transforming 8-αhydroxyethyl caffeine into the corresponding 8-α-chloroethyl caffeine by the action of a suitable chlorinating agent such as thionyl chloride, reacting the product so obtained in a suitable solvent such as anhydrous dimethylformamide at a temperature from 40° to 110° C and for a period of time from 1 to 5 hours with the sodium or potassium salt of a nicotinic acid of the formula:

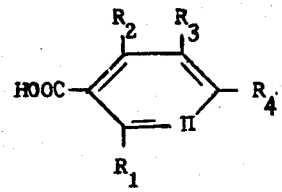

where $R_1$, $R_2$, $R_3$ and $R_4$ have the above-mentioned meanings, and crystallizing the resulting product from a suitable solvent, such as ethanol. These new compounds have broncholitic activity.

16 Claims, No Drawings

CAFFEINE DERIVATIVES

The present invention relates to new caffeine derivatives and to a process for their preparation.

More particularly, the main objects of the present invention are the provision of caffeine derivatives substituted in position eight of the caffeine moiety, and having the general formula:

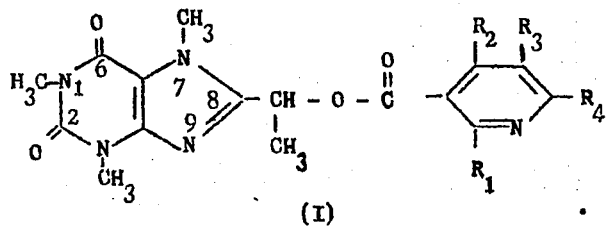

(I)

where $R_1$, $R_2$, $R_3$ and $R_4$ are selected from the group consisting of hydrogen, chlorine, bromine, an alkyl or an alkoxy radical containing from 1 to 4 carbon atoms; and a process for the preparation of such caffeine derivatives.

These new compounds have a remarkable broncholitic activity. They are prepared according to the following scheme:

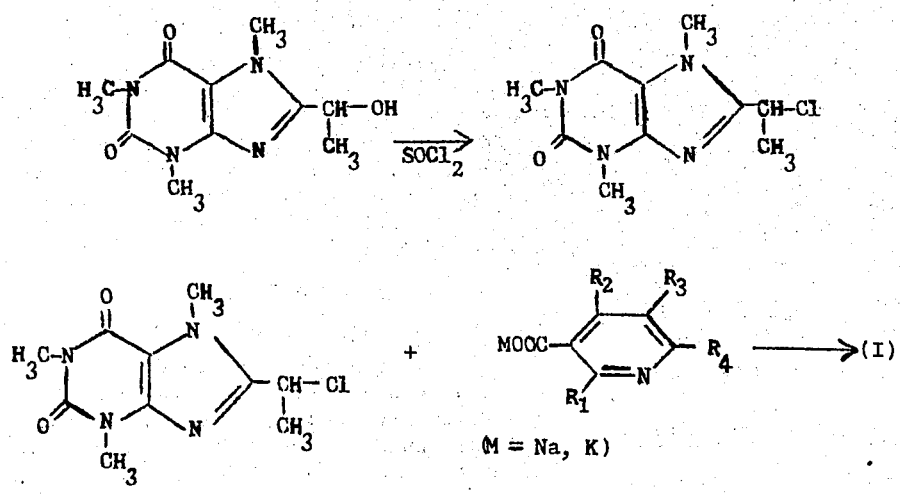

(M = Na, K)

More particularly, 8-α-hydroxyethylcaffeine (*Arch. der Pharmazie*, 289, 453, 1956) is transformed by means of a suitable chlorinating agent, such as thionyl chloride, under shaking for 6 hours into the corresponding 8-α-chloroethylcaffeine. This latter (which itself is a new compound), dissolved in a suitable solvent such as anhydrous dimethylformamide, is reacted with the sodium or potassium salt of a nicotinic acid having the general formula:

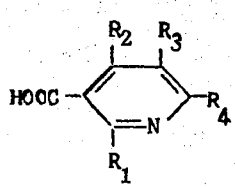

wherein $R_1$, $R_2$, $R_3$ and $R_4$ have the above-mentioned meanings.

This reaction takes place at a temperature from 40°–110° C and for a period of from 1 to 5 hours.

At the end of the reaction, the mixture is filtered and the solvent evaporated off. The residue is washed first with water, then with sodium bicarbonate, and again with water. The desired final product is then crystallized from a suitable solvent such as ethanol.

The products of the present invention display good broncholitic activity, they do not cause undesired collateral effects, and are effective in bronchial asthma therapy. More particularly, two of the new compounds within the broad subclass of compounds falling within the scope of the present invention have been tested; viz., 8-[α-(2,4-dimethylnicotinoyloxy)-ethyl] -and 8-[α-(nicotinoyloxy)-ethyl]-caffeine monohydrochloride.

The broncholitic activity of these compounds has been evaluated in the awake guinea-pig and expressed as the percentage protection against bronchial spasm caused by a broncho-constrictor aerosol of histamine hydrochloride (Siegmund, Granger, et al., *J. Pharm. Exp. Therap.* 1947, 90, 254; Armitage et al., *Brit. J. Pharmacol.* 1961, 16, 59).

As comparison compound, Aminophilline has been used (theophilline + ethylenediamine) which has been employed for some time in bronchial asthma therapy, in spite of its undesired secondary effects, i.e., excitement caused by caffeine and irritation of the gastric mucous membrane.

The data summarized in the following Table 1 show that the compounds of the present invention have a broncholitic activity higher than that of Aminophilline when administered by the intraperitoneal (i.p.) route.

Table 1

| Substance | Dose mg/kg | Protection percentage from the spasm caused by histamine | | Survivals rates after 48 hours of the treatment |
|---|---|---|---|---|
| | | i.p. route after 30' of the administration | oral route after 60' of the administration | Oral route |
| Aminophilline | 50 | 24 | 14 | 84 |
| | 75 | 80 | 31 | 84 |
| | 100 | 100 | 92 | 50 |
| | 150 | 100 | 95 | 10 |
| | 200 | — | — | — |
| 8-[α-(nicoti-noyloxy)-ethyl]-caffeine monohydrochloride (386/770) | 25 | 35 | — | — |
| | 50 | 38 | — | — |
| | 75 | 94 | 13 | 100 |
| | 150 | — | 26 | 100 |
| | 300 | — | 65 | 100 |
| 8-[α-(2,4-dimethylnicotinoyloxy)-ethyl]-caffeine monohydrochloride (386/986) | 25 | 22 | — | — |
| | 50 | 39 | — | — |
| | 75 | 85 | 39 | 100 |
| | 150 | — | 54 | 100 |
| | 300 | — | 80 | 100 |

Also the new compounds of the present invention show good bronchollitic activity by the oral route. From the values of $LD_{50}$ reported below in Table 2, it clearly appears that the new compounds are less toxic than Aminophilline when they are tested for acute toxicity in the examined animals. Furthermore, guinea-pigs treated with Aminophilline and subjected to the test for the evaluation of broncholitic activity show a tardy high mortality which is completely absent even at high dosages in the animals treated with the compounds of Table 1.

Table 2

(Acute toxicity.)

| Substance | $LD_{50}$ mg/kg | | | |
|---|---|---|---|---|
| | Guinea-pig | | Mouse | |
| | o) i.p. | x) per os | o) i.p. | x) per os |
| Aminophillin | 130 | 220 | 220 | 400 |
| 8-[α-(nicotinoyloxy)-ethyl]-caffeine | 220 | 440 | 445 | 520 |
| 8-[α-(2,4-dimethylnicotinoyloxy)-ethyl]-caffeine | — | — | 320 | 500 | o) compound dissolved in physiological salt solution.
x) compound suspended in 5% arabic gum.

The undesired action on the central nervous system has been evaluated with the strengthening of the andiogenic convulsions test in the mouse (Werboff et coll., *Amer. J. Physiol.*, 201, 830, 1961). As is well known, the theophilline derivatives potentiate the effects of the acoustic stimulus (motory agitation, clonic and tonic convulsions which may lead to the death of the animals). From the data presently available, it appears that Aminophilline causes a remarkable strengthening of the effects of the acoustic stimulus at the intraperitoneal dose of 50 mg/kg and moreover causes the death of the 50% treated animals. The two specific compounds falling within the scope of the present invention when tested under the same conditions, until the dose i.p. 150 mg/kg, do not cause the death of any treated animals.

The following examples will serve additionally to illustrate the invention without limiting it.

EXAMPLE 1

8-α-Chloroethyl caffeine 10 g of 8-α-hydroxyethylcaffeine (*Arch. der Pharmazie*, 289, 453, 1956) are added and under shaking with 100 ml of thionyl chloride. After 6 hours of reflux, the excess of reagent is evaporated to dryness under reduced pressure and the solid residue washed with petroleum ether. Nearly pure 8-α-chloroethylcaffeine is obtained with a quantitative yield, melting at 190° C from anhydrous benzene.

EXAMPLE 2

8-[α-(nicotinoyloxy)-ethyl]-caffeine 2.57 g of 8-α-chloroethylcaffeine are dissolved in 25 ml of anhydrous dimethylformamide, to which 2.98 g of dry potassium nicotinate are added. The mixture is heated under shaking at 100° C for 1 hour, then filtered off and the filtrate evaporated under reduced pressure. The residue, after washing with water, gives 3.1 g of slightly crude product which is purified by crystallization from 95% ethanol : m.p. (EtOH) 160° C. The monohydrochloride melts at 200°–210° C.

EXAMPLE 3

8-[α-(5-bromonicotinoyloxy)-ethyl]-caffeine 2.87 g of 8-α-chloroethylcaffeine are dissolved in 30 ml of anhydrous dimethylformamide, and then 2.7 g of the sodium salt of dry 5-bromonicotinic acid are added.

The mixture is heated under shaking at 50° C for 4.5 hours, and then evaporated to dryness under reduced pressure. The residue oil is heated with chloroform and aqueous sodium bicarbonate.

The organic phase is washed with aqueous sodium bicarbonate, and then with water, and then is dried and evaporated under reduced pressure. A solid (3 g) prevalently consisting of the desired product is obtained. M.P. 140°–150° C after twofold crystallization from ethanol absolute.

EXAMPLE 4

8-[α-(2,4-dimethylnicotinoyloxy)-ethyl]-caffeine 1.54 g of 8-α-chloroethylcaffeine are dissolved in 15 ml of anhydrous dimethylformamide, and 1.75 g of the sodium salt of dry 2,4-dimethylnicotinic acid are then added.

The mixture is heated under shaking at 100° C for 4 hours, and then dried to dryness under reduced pressure.

The solid residue washed with water gives 2 g of a slightly crude product which is purified by crystallization from 95% ethanol. M.P. 164° C. The monohydrochloride melts at 195° C.

EXAMPLE 5

Operating as described in the previous examples, the following additional caffeine derivatives have been synthesized:

8-[α-(2,6-dimethylnicotinoyloxy)-ethyl]-caffeine: m.p. 160° C (hydrochloride: m.p. 200°–210° C)

8-[α-(2-methoxynicotinoyloxy)-ethyl]-caffeine: m.p. 178° C

8-[α-(5-methoxynicotinoyloxy)-ethyl]-caffeine

8-[α-(6-methylnicotinoyloxy)-ethyl]-caffeine: m.p. 192° C (hydrochloride: m.p. 165°–180° C)

8-[α-(2-chloronicotinoyloxy)-ethyl]-caffeine: m.p. 152° C

8-[α-(2.4-dichloro-6-methylnicotinoyloxy)-ethyl]-caffeine: m.p. 168° C

8-[α-(2,4-dimethoxy-6-methylnicotinoyloxy)-ethyl]-caffeine: m.p. 208°–210° C

8-[α-(2,6-dimethyl-4-methoxynicotinoyloxy)-ethyl]-caffeine: m.p. 135°–138° C (hydrochloride: 160°–165° C)

8-[α-(2,4-dimethyl-6-methoxy-nicotinoyloxy)-ethyl]-caffeine

8-[α-(2,6-dimethyl-4-chloronicotinoyloxy)-ethyl]-caffeine: m.p. 158° C

8-[α-2-methoxy-4-chloro-6-methylnicotinoyloxy)-ethyl]-caffeine: m.p. 168°–170° C 8-[α-(5-methylnicotinoyloxy)-ethyl]-caffeine: m.p. 110° C (hydrochloride: 190°–195° C)

What is claimed is:

1. A compound having broncholitic activity and having the general formula:

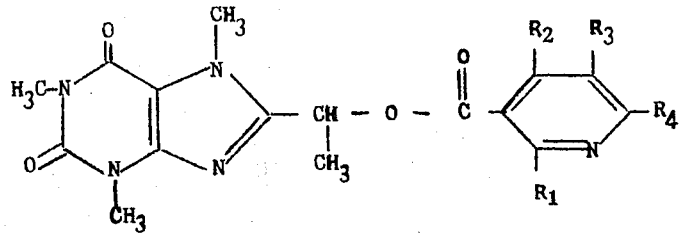

where $R_1$, $R_2$, $R_3$ and $R_4$ are selected from the group consisting of hydrogen, chlorine, bromine, an alkyl or an alkoxy radical having from 1 to 4 carbon atoms.

2. A compound according to claim 1 which is 8-[α-(nicotinoyloxy)-ethyl]-caffeine.

3. A compound according to claim 1 which is 8-[α-(5-bromonicotinoyloxy)-ethyl]-caffeine.

4. A compound according to claim 1 which is 8-[α-(2,4-dimethylnicotinoyloxy)-ethyl]-caffeine.

5. A compound according to claim which is which 8-[α-(2,6-dimethylnicotinoyloxy)-ethyl]-caffeine.

6. A compound according to claim 1 which is 8-[α-(2-methoxynicotinoyloxy)-ethyl]-caffeine.

7. A compound according to claim 1 which is 8-[α-(5-methoxynicotinoyloxy)-ethyl]-caffeine.

8. A compound according to claim 1 which is 8-[α-(6-methylnicotinoyloxy)-ethyl]-caffeine.

9. A compound according to claim 1 which is 8-[α-(2-chloronicotinoyloxy)-ethyl]-caffeine.

10. A compound according to claim 1 which is 8-[α-(2,4-dichloro-6-methylnicotinoyloxy)-ethyl]-caffeine.

11. A compound according to claim 1 which is 8-[α-(2,4-dimethoxy-6-methylnicotinoyloxy)-ethyl]-caffeine.

12. A compound according to claim 1 which is 8-[α-(2,6-dimethyl-4-methoxynicotinoyloxy)-ethyl]-caffeine.

13. A compound according to claim 1 which is 8-[α-(2,4-dimethyl-6-methoxynicotinoyloxy)-ethyl]-caffeine.

14. A compound according to claim 1 which is 8-[α-(2,6-dimethyl-4-chloronicotinoyloxy)-ethyl]-caffeine.

15. A compound according to claim 1 which is 8-[α-(2-methoxy-4-chloro-6-methylnicotinoyloxy)-ethyl]-caffeine.

16. A compound according to claim 1 which is 8-[α-(5-methylnicotinoyloxy)-ethyl]-caffeine.

* * * * *